(12) United States Patent
Kurtz

(10) Patent No.: US 10,292,866 B2
(45) Date of Patent: *May 21, 2019

(54) METHOD OF TRANSPLANTING A CORNEA

(71) Applicant: AMO Development, LLC, Santa Ana, CA (US)

(72) Inventor: Ronald M. Kurtz, Irvine, CA (US)

(73) Assignee: AMO Development, LLC, Santa Ana, CA (US)

(*) Notice: Subject to any disclaimer, the term of this patent is extended or adjusted under 35 U.S.C. 154(b) by 180 days.

This patent is subject to a terminal disclaimer.

(21) Appl. No.: 15/212,130

(22) Filed: Jul. 15, 2016

(65) Prior Publication Data

US 2016/0324687 A1     Nov. 10, 2016

Related U.S. Application Data

(63) Continuation of application No. 11/369,197, filed on Mar. 6, 2006, now Pat. No. 9,402,714.

(51) Int. Cl.
*A61F 9/011* (2006.01)
*A61F 9/008* (2006.01)
*A61F 2/14* (2006.01)

(52) U.S. Cl.
CPC .......... *A61F 9/0081* (2013.01); *A61F 2/142* (2013.01); *A61F 9/00831* (2013.01); *A61F 2/14* (2013.01); *A61F 9/00827* (2013.01); *A61F 9/00836* (2013.01); *A61F 2009/00853* (2013.01); *A61F 2009/00872* (2013.01); *A61F 2009/00893* (2013.01)

(58) Field of Classification Search
CPC .......... A61F 2/14; A61F 2/142; A61F 9/0081; A61F 9/00831; A61F 9/00853; A61F 9/00836; A61F 2009/00872; A61F 9/0827; A61F 2009/00873
USPC .............................. 606/4–6, 10–13; 128/898
See application file for complete search history.

(56) References Cited

U.S. PATENT DOCUMENTS

| | | | |
|---|---|---|---|
| 4,732,148 A | 3/1988 | L'Esperance, Jr. | |
| 5,549,632 A | 8/1996 | Lai | |
| 5,964,748 A | 10/1999 | Peyman | |
| 5,984,916 A | 11/1999 | Lai | |
| 6,110,166 A | 8/2000 | Juhasz | |
| 6,805,694 B2 | 10/2004 | Donitzky | |

(Continued)

FOREIGN PATENT DOCUMENTS

WO    2004105585 A2    12/2004

OTHER PUBLICATIONS

International Search Report for Application No. PCT/US2007/05051, dated Nov. 2, 2007, 1 page.

*Primary Examiner* — David Shay
(74) *Attorney, Agent, or Firm* — Johnson & Johnson Surgical Vision, Inc.

(57) ABSTRACT

A method of transplanting a cornea from a donor to a recipient is disclosed. An undercut is incised within stromal tissue of the donor cornea. Following formation of the undercut, the donor cornea is grafted onto a recipient. The undercut may be formed before or after the cornea is removed from the donor, and is preferably formed by photoaltering the stromal tissue using a laser. A sidecut may also be incised in the donor cornea, thereby forming a corneal flap, prior to grafting. In addition, a corneal section may be excised from the donor cornea using a trephine, a laser, or other appropriate surgical equipment.

18 Claims, 2 Drawing Sheets

(56) References Cited

U.S. PATENT DOCUMENTS

| | | | |
|---|---|---|---|
| 7,041,114 B2* | 5/2006 | Dan | A61F 9/00781 128/898 |
| 9,402,714 B2* | 8/2016 | Kurtz | A61F 9/00831 606/5 |

* cited by examiner

METHOD OF TRANSPLANTING A CORNEA

This application is a continuation application under 35 USC § 120 of U.S. patent application Ser. No. 11/369,197, filed Mar. 6, 2006, now pending, the entire contents of which are incorporated herein by reference.

BACKGROUND OF THE INVENTION

1. Field of the Invention

The field of the present invention is techniques for transplanting corneas.

2. Background

Many different diseases or conditions of the cornea exist which completely or effectively rob those who suffer from such diseases or conditions of vision. Fortunately, corneal transplant procedures, which are becoming more commonplace, are capable of substantially restoring lost vision. One drawback to such procedures is that acuity of vision cannot be wholly restored without use of corrective lenses. Further, for a substantial time following transplantation, the condition of the grafted cornea is too delicate to undergo certain aspects of Laser Assisted In-Situ Keratomileusis ("LASIK") to correct the vision of the recipient. This is generally because corneas comprise avascular tissue, in which the healing process can take many months, and the use of a microkeratome or a suction device on the cornea can damage the grafted tissue if it is not fully healed.

SUMMARY OF THE INVENTION

The present invention is directed towards a method of transplanting a cornea from a donor to a recipient. The cornea is processed prior to grafting so that the LASIK procedure may be performed on the grafted cornea without placing the donated tissue at significant risk of damage.

In a first separate aspect of the present invention, an undercut is incised within stromal tissue of the donor cornea. The incised donor cornea is thereafter grafted onto the eye of a recipient.

In a second separate aspect of the present invention, which builds upon the first separate aspect, a sidecut is incised in the donor cornea such that the combination of the sidecut and the undercut create a corneal flap.

In a third separate aspect of the present invention, which builds upon the first separate aspect, a corneal section is excised from the donor cornea, and the corneal section is grafted onto the recipient's eye. The corneal section may be smaller than and at least partially include the undercut, or it may entirely include the undercut. The corneal section may be excised using a trephine, a laser, or other appropriate surgical equipment.

In a fourth separate aspect of the present invention, the corneal processing may occur before or after the donor cornea is removed from the donor.

In a fifth separate aspect of the present invention, the corneal processing includes photoaltering stromal tissue within the donor cornea using a laser.

In a sixth separate aspect of the present invention, any of the foregoing aspects may be employed in combination.

Accordingly, it is an object of the present invention to provide an improved method of transplanting a cornea. Other objects and advantages will appear hereinafter.

BRIEF DESCRIPTION OF THE DRAWINGS

In the drawings, wherein like reference numerals refer to similar components.

DETAILED DESCRIPTION OF THE PREFERRED EMBODIMENTS

Figure 1A:
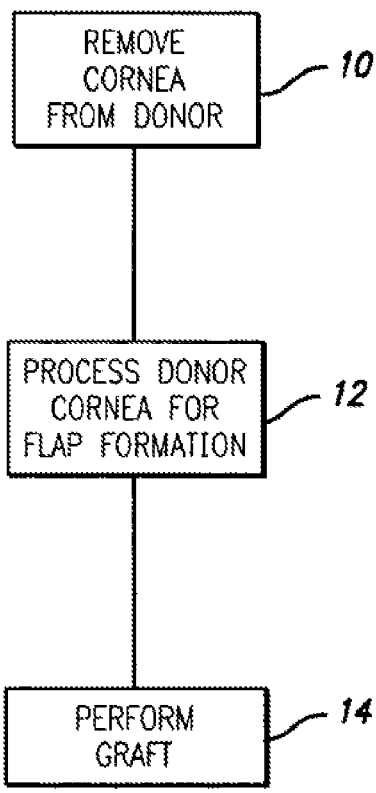
FIGS. 1A-B are flowcharts which illustrate different sequences of steps for processing and transplanting a cornea.
Figure 1B:
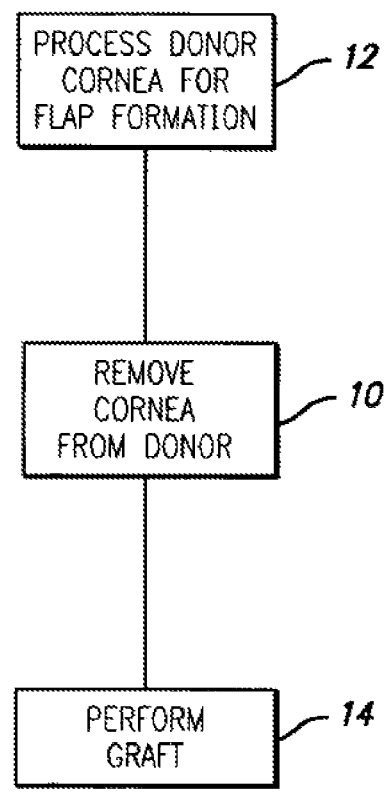

Turning in detail to the drawings, FIGS. 1A & 1B illustrate two different sequences for performing the corneal transplant. In the sequence shown in FIG. 1A, the donor cornea is first removed from the donor 10, processed for flap formation 12, then grafted onto the recipient's eye 14. The techniques used for grafting the donor cornea onto the recipient's eye are well known and thus not described in detail. In the sequence shown in FIG. 1B, the donor cornea is processed for flap formation 12 before being removed from the donor 10. By creating a flap in the donor cornea prior to performing the graft, the corneal flap can be lifted and access gained to the underlying stromal tissue after the donor cornea is grafted onto the recipient's eye. This allows the stroma to be appropriately shaped to correct, via common LASIK procedures, any myopia or hyperopia present in the recipient's vision following the transplant. In addition, because the cornea is avascular, the corneal flap may be lifted for the LASIK procedure immediately following the transplant or for a period of six months or more thereafter.

Figure 2A:
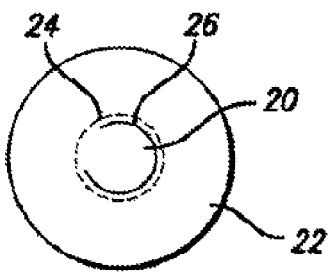
FIG. 2A is an elevation view of a cornea and corneal flap.
Figure 2B:
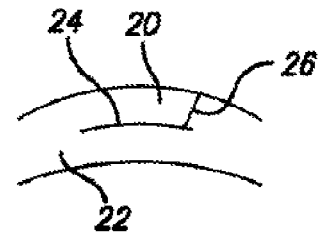
FIG. 2B is a sectional view of a cornea and corneal flap.

FIGS. 2A & 2B illustrate a corneal flap 20 formed in a donor cornea 22 during the transplantation process. As indicated above, the corneal flap 20 is formed prior to the time the donor cornea 22 is grafted onto the recipient's eye. The corneal flap 20 is formed by an undercut 24 within stromal tissue and a sidecut 26 between the undercut 24 and the anterior surface of the donor cornea 22. U.S. Pat. No. 5,549,632 to Lai, U.S. Pat. No. 5,984,916 to Lai, and U.S. Pat. No. 6,110,166 to Juhasz, the disclosures of which are incorporated herein by reference in their entirety, disclose methods for incising the cornea using a laser to photoalter the corneal tissue, thereby forming the corneal flap. As is evidenced from the aforementioned patents, when an applanation lens is employed, the undercut 24 will generally be a planar incision within the stroma. If a curved contact lens is employed, the undercut will generally be a radially defined incision. The undercut 24, however, may have any appropriate shape or form for formation of the corneal flap.

The following describes three different techniques which may be used to form the corneal flap in the donor cornea prior to implantation.

All Laser Procedure

Figure 3A:
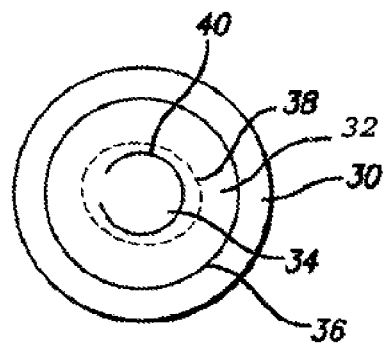
FIGS. 3A-C illustrate different techniques for processing the donor cornea.

The donor cornea 30 for this preferred technique is illustrated in FIG. 3A. The corneal section 32 is first formed in, but not necessarily excised from, the donor cornea 30, then the corneal flap 34 is incised in the corneal section 32. All incisions for this technique are performed with a laser. To accomplish this, three incisions are made, preferably in the following order. The first incision 36 is made to create the corneal section 32. This first incision 36 enables the corneal section 32 to be separated from the rest of the donor cornea 30, but it does not result in separation. Separating the corneal section 32 from the donor cornea 30 at this juncture is discretionary. The second incision is the undercut 38, and the third incision is the sidecut 40, both of which are needed for formation of the corneal flap 34.

Before these incisions are made, it is beneficial to anticipate needs that arise during and following the grafting process and during the LASIK procedure to be performed on the recipient. For example, with regard to the relative size of the corneal flap 34 as compared to the size of the corneal section 32, it may be desirable to make the corneal section 32 be sufficiently larger than the corneal flap 34 to allow for placement of a suture in the corneal section 32 once it is grafted onto the recipient's eye. Insufficient space may result in the corneal flap 34 being accidentally secured by a suture. By way of another example, the size of the recipient's eye and pupil should be taken into consideration for the size of the corneal flap 34.

By making all incisions with a laser, they may all be done sequentially without requiring repositioning of the donor cornea during the excision and flap-forming processes. In addition, this simplifies placement of the flap 34 within the corneal section 32, so that the flap 34 is positioned appropriately on the recipient's eye for the subsequent LASIK procedure. Having the flap 34 centered on the corneal section 32 is preferred.

It may also be desirable to place a mark on the corneal section 32, using the incising laser, to indicate the location of the hinge portion of the flap. This facilitates subsequent location and lifting of the flap for the LASIK procedure. Other types of markers, such as ink, one or more sutures, or other physical marks, may also be used to indicate the location of the hinge portion of the flap. Such marking may be employed regardless of the technique used to prepare the cornea for implantation.

As previously mentioned, the corneal section 32 and flap 34 may be created before or after the donor cornea has been removed from the donor. Processes for incising a cornea with a laser are well known regardless of when the procedure is performed. This is true whether the process is done before the donor cornea is removed from the donor, whether the entire eye is harvested during the donation procedure, or whether the cornea alone is harvested. In the latter instance, an artificial anterior chamber, a device well known in the art, is used to mount the corneal tissue for further processing.

Laser with Trephine (Method 1)

This technique is similar to the all laser technique, with the difference being that the undercut 38 and sidecut 40 are first incised in the donor cornea for formation of the corneal flap 34. After these two incisions are made, then the corneal section 32 is stamp-cut out of the donor cornea 30 using a trephine. The resulting corneal section 32 is the same as the one depicted in FIG. 3A.

Laser with Trephine (Method 2)

Figure 3B:
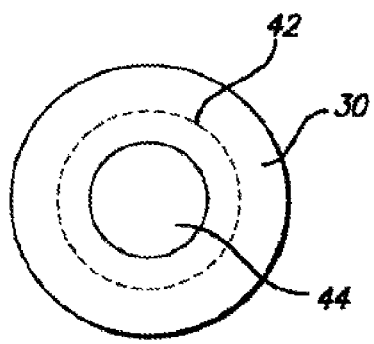
Figure 3C:
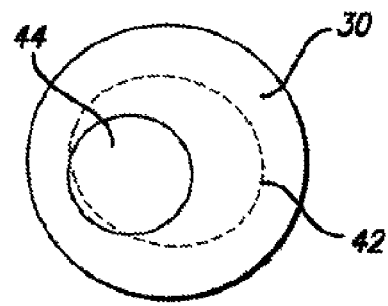

This last technique has two variations, which are depicted in FIGS. 3B & 3C. In the variation shown in FIG. 3B, an undercut 42 is incised in the donor cornea 30 such that the undercut 42 is larger than the corneal section needed for the graft. Following incision of the undercut 42, a trephine is used to stamp-cut the corneal section 44 out of the donor cornea 30. This corneal section 44 may be entirely within the undercut 42, as shown in FIG. 3B, or it may include a portion of the donor cornea 30 that does not include the undercut 42, as shown in FIG. 3C. In the former case, a suture or two may be required on one side of the corneal section 44 to maintain the integrity of the corneal section 44 and to form the hinge portion of the corneal flap. In the latter case, the part of the corneal section 44 that does not include the undercut 42 forms the hinge portion of the corneal flap.

Thus, a method of transplanting a cornea is disclosed. While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A method of transplanting a corneal section from a donor to a recipient in preparation for performing a Laser Assisted In-Situ Keratomileusis ("LASIK") procedure, the method comprising:
   incising an undercut within stromal tissue of a donor cornea of a donor, wherein the donor cornea has an anterior surface, and wherein the undercut is incised posterior to the anterior surface of the donor cornea so that underlying stromal tissue of the donor cornea is disposed posterior to the undercut and overlying stromal tissue of the donor cornea is disposed anterior to the undercut;
   incising a sidecut in the donor cornea such that the combination of the sidecut and the undercut create a corneal flap having a hinge portion, the underlying stromal tissue connected with the overlying stromal tissue via the hinge portion on one side of the corneal flap, the underlying stromal tissue unconnected with the overlying stromal tissue on a second side of the corneal flap opposing the first side;
   after forming the corneal flap in the donor cornea, excising a corneal section containing the corneal flap from the donor cornea; and
   grafting the incised corneal section onto an eye of a recipient;
   wherein, after the donor corneal section is grafted onto the eye of the recipient, the underlying stromal tissue of the donor corneal section is located immediately below the undercut and the overlying stromal tissue of the donor corneal section is located immediately above the undercut, and lifting of the corneal flap of the donor corneal section provides access for performing the LASIK procedure on the underlying stromal tissue of the donor corneal section that has been grafted onto the eye of the recipient.

2. The method of claim 1, wherein at least one of the undercut incising step and the sidecut incising step includes incising the cornea by photoaltering the stromal tissue using a laser.

3. The method of claim 1, wherein the excising of the corneal section includes excising the corneal section using a laser.

4. The method of claim 1, wherein the LASIK procedure is performed immediately following the grafting step.

5. The method of claim 1, wherein following the grafting step, the method further includes lifting the corneal flap, ablating a portion of the underlying stromal tissue of the donor cornea, and repositioning the corneal flap to cover the ablated underlying stromal tissue.

6. A method of transplanting a cornea from a donor to a recipient in preparation for performing an ophthalmic procedure, the method comprising:
   incising an undercut within stromal tissue of a donor cornea, wherein the donor cornea has an anterior surface, and wherein the undercut is incised posterior to the anterior surface of the donor cornea so that underlying stromal tissue of the donor cornea is disposed posterior to the undercut and overlying stromal tissue of the donor cornea is disposed anterior to the undercut;
   incising a sidecut in the donor cornea such that the combination of the sidecut and the undercut create a corneal flap having a hinge portion, the underlying stromal tissue connected with the overlying stromal tissue via the hinge portion on one side of the corneal flap, the underlying stromal tissue unconnected with the overlying stromal tissue on a second side of the corneal flap opposing the first side; and grafting the incised donor cornea including the corneal flap onto an eye of a recipient;

wherein, after the incised donor cornea is grafted onto the eye of the recipient, the underlying stromal tissue of the donor cornea is located immediately below the undercut and the overlying stromal tissue of the donor cornea is located immediately above the undercut, and lifting of the corneal flap of the donor cornea provides access for performing the ophthalmic procedure on the underlying stromal tissue of the donor cornea.

7. The method of claim 6, wherein at least one of the undercut incising step or the sidecut incising step is performed after the donor cornea is removed form the donor.

8. The method of claim 6, wherein at least one of the undercut incising step or the sidecut incising step includes incising the cornea by photoaltering the stromal tissue using a laser.

9. The method of claim 6, wherein the ophthalmic procedure is performed immediately following the grafting step.

10. The method of claim 6 further comprising, prior to the grafting step, trephining a corneal section from the incised cornea.

11. The method of claim 10, wherein the corneal section is entirely within the undercut.

12. The method of claim 10, wherein the corneal section is smaller than and at least partially includes the undercut.

13. The method of claim 12, wherein the corneal section includes a portion of the undercut sufficient to form a flap.

14. A method of transplanting a cornea from a donor to a recipient in preparation for performing an ophthalmic procedure, the method comprising:

incising an undercut within stromal tissue of a donor cornea by photoaltering the stromal tissue using a laser, wherein the donor cornea has an anterior surface, and wherein the undercut is incised posterior to the anterior surface of the donor cornea so that underlying stromal tissue of the donor cornea is disposed posterior to the undercut and overlying stromal tissue of the donor cornea is disposed anterior to the undercut;

trephining a corneal section from the incised cornea, wherein the corneal section is entirely within the undercut;

placing at least one suture in at least one side of the corneal section, wherein the at least one suture in at least one side of the corneal section acts as a hinge portion forming a corneal flap;

grafting the trephined cornea section including the corneal flap onto an eye of a recipient;

wherein, after the incised donor cornea is grafted onto the eye of the recipient, the underlying stromal tissue of the donor cornea is located immediately below the undercut and the overlying stromal tissue of the donor cornea is located immediately above the undercut, and lifting of the corneal flap of the donor cornea provides access for performing the ophthalmic procedure on the underlying stromal tissue of the donor cornea.

15. The method of claim 14, wherein the undercut incising step is performed after the donor cornea is removed form the donor.

16. The method of claim 14, wherein the ophthalmic procedure is performed immediately following the grafting step.

17. The method of claim 14, wherein the ophthalmic procedure is a Laser Assisted In-Situ Keratomileusis ("LASIK") procedure.

18. The method of claim 14, wherein following the grafting step, the method further includes lifting the corneal flap, ablating a portion of the underlying stromal tissue of the donor cornea, and repositioning the corneal flap to cover the ablated underlying stromal tissue.

* * * * *